United States Patent [19]
Herman et al.

[11] Patent Number: 5,629,212
[45] Date of Patent: May 13, 1997

[54] CHLORIDE MONITORING APPARATUS

[75] Inventors: Patrick Herman, Droue sur Drouette; Jean M. Faure, Cornas; Philippe Engelberg, Carrieres sur Seine, all of France; Michel Mercusot, Antwerp (Hoboken), Belgium

[73] Assignee: W.R. Grace & Co.-Conn., New York, N.Y.

[21] Appl. No.: 466,486

[22] Filed: Jun. 6, 1995

[30] Foreign Application Priority Data

Jan. 30, 1995 [GB] United Kingdom ............... 9501732

[51] Int. Cl.$^6$ .................................................. G01N 27/26
[52] U.S. Cl. ........................ 436/125; 436/55; 436/60; 436/124; 436/149; 436/150; 436/151; 436/163; 436/175; 436/178; 204/401; 204/416
[58] Field of Search ..................... 436/124, 125, 436/149, 150, 151, 60, 50, 163, 175, 178; 204/153.13; 423/502, 507; 208/108

[56] References Cited

U.S. PATENT DOCUMENTS

| 4,120,779 | 10/1978 | Baird, Jr. et al. | 208/108 |
| 4,942,133 | 7/1990 | Pauly et al. | 436/125 |
| 4,959,202 | 9/1990 | Minet et al. | 423/502 |
| 4,975,156 | 12/1990 | Wismer | 203/39 |
| 5,367,102 | 11/1994 | Janssens et al. | 570/164 |

FOREIGN PATENT DOCUMENTS

| 2342496 | 2/1976 | France | G01N 27/46 |
| A-2492531 | 4/1982 | France | G01N 33/18 |
| 2624975 | 12/1987 | France | G01N 35/00 |
| A-1497669 | 1/1978 | United Kingdom | G01N 27/46 |

OTHER PUBLICATIONS

International Search Report for PCT/US 96/00805 dated Jun. 7, 1996, 6 pages.

Derwent abstract for FR-A-2492531 cited above.

*Primary Examiner*—Harold Pyon
*Attorney, Agent, or Firm*—Alexander D. Ricci; Matthew W. Smith

[57] ABSTRACT

A chloride analyzer includes an inlet valve and filters for process water to be analyzed, as well as a pH electrode to verify the pH value of the incoming liquid before further treatment. A stripper bubbles stripping air through the process water to remove hydrocarbons and hydrogen sulfide therefrom, and the discharge line from said stripper feeds a reaction vessel to which also reagent from a supply vessel is passed. After a suitable reaction time, optionally followed by a further air stripping operation through air supply line, the reaction products are fed via line to an ionometry measuring cell where chloride analysis is carried out using a specific ion selective electrode.

10 Claims, 5 Drawing Sheets

CHLORIDE MONITORING APPARATUS

FIELD OF THE INVENTION

The present invention relates to a method of and apparatus for monitoring the presence of chlorides in a liquid, discontinuously but at frequent intervals. One particular application of the method and apparatus is in the analyzing of process waters containing sulphides, hydrocarbons and other pollutants in the presence of the chlorides being monitored, for example with a view to controlling the dosing of a conditioning additive to the crude or to the process water.

PRIOR ART

In the oil refining and petrochemicals industries, hydrochloric acid commonly occurs and is a corrosive product found in most of the process waters. As disclosed in U.S. Pat. No. 4,942,133, once the chloride ion content is above 10 ppm, there is a very pronounced increase in the corrosion in the water circuits. It is therefore important to know the chloride concentration so analysis of the chloride content therefore gives a measure of the corrosiveness of the process water and enables effective control to be exercised over the addition of conditioning additives such as caustic, corrosion inhibitors, or neutralising agents. Unfortunately, sulfides are often also present in those process waters, and the presence of the sulfides would hamper the analysis of the chlorides so it is necessary first to transform any sulfides present into products which do not interfere with the chloride measurement, and preferably to remove them before measurement occurs.

In control laboratories of processing plants such as the oil refining and petrochemical industries, in particular in connection with hydrocarbon distillation columns such as columns for distilling crude petroleums, the laboratory analysis of the chloride content is carried out usually once a day, and the analysis itself takes a significant time, of the order of 2 hours. Given that the sample may itself take a long time to reach the laboratory after having been collected, the results of the analysis are usually available only 12 hours after the sampling and sometimes only 30 hours after the sampling, which causes extreme difficulty in applying an on-line control technique. Proper corrosion protection of process water plant requires a frequency greater than once per 24 hours, and also a response time much less than 30 hours.

U.S. Pat. No. 4,942,133 discloses a continuous process.

FR-A-2342496 discloses a continuous process in which the monitoring of halide ions in the presence of hydrogen sulphide ($H_2S$) and other sulphides is effected by first destroying the $H_2S$ and/or other sulphides by oxidation.

OBJECTS OF THE INVENTION

It is an object of the present invention to provide for the analysis of the chloride content in process waters whether or not the presence of sulfides occurs, and preferably to effect the analysis using automatic on-line equipment.

It is a further object of the present invention to provide an on-line chloride analyzer which can automatically measure the chloride content of any process waters, with an adjustable frequency, and which can adjust the injection of a chemical, such as a caustic or a corrosion inhibitor or a neutralizing agent, as a conditioning additive either to control the chlorides content within a target range or to protect the system against corrosion.

SUMMARY OF THE INVENTION

Accordingly, one aspect of the present invention provides a process for analyzing the chloride content of a liquid, comprising: stripping hydrocarbons and hydrogen sulphide from a batch of the liquid; reacting the liquid batch with an oxidizing reagent to oxidize $HS^-$ and $S^-$ ions into sulfate ions, and to lower the pH of the liquid to be analysed; and then analysing the chloride content of the products of the reaction by ionometry.

Preferably the process may include the steps of adding a conditioning additive to the liquid, and adjusting the dose of the conditioning additive in response to the chloride concentration determined.

A second aspect of the present invention provides apparatus for analyzing the chloride content of liquid, comprising a stripper to receive said liquid to be analyzed and to strip compounds from the liquid by passing stripping air through the liquid; a reactor vessel connected to said stripper to receive the stripped liquid and also connected to a supply of reagent for reaction with said liquid; an ionometry measuring cell connected to receive the reaction products from said reactor vessel; air propulsion for movement of the liquid and reagent through the apparatus propulsion, thereby avoiding the need for pumps in contact with the liquid being analyzed; and control means for controlling the charging and discharging of successive batches of liquid in said stripper, the reaction in said reactor vessel, and the ionometry operation in said ionometry cell, all in batchwise manner.

BRIEF DESCRIPTION OF THE DRAWINGS

In order that the present invention may more readily be understood the following description is given, merely by way of example, with reference to the accompanying drawings, in which.

DETAILED DESCRIPTION OF THE PREFERRED EMBODIMENT

In implementing the method in accordance with the present invention, a continuous flow of process water from a refinery or petrochemical processing plant is bled from the plant, filtered, and then stripped of its residual hydrocarbons and hydrogen sulphide, using air. A sample batch of this stripped water is then taken, and is conveyed to a reactor where a single reagent is added in a quantity related to the volume of the sample batch.

In the present embodiment a single reagent is used, in this case an aqueous solution of nitric acid (1 mole/l) and sodium bromate (0.1 mole/l). This reaction both (a) oxidizes the $HS^-$ and $S^-$ ions to $SO_4^-$ ions which will not interfere with the measurement of the chloride ions, and (b) adjusts the pH to the desired range for achieving optimum accuracy in the chloride analysis.

Other reagents may be used, for example, any oxidant which will oxidize sulfides but not chlorides could work. Examples include a chromate ($CrO_7^{--}$) or a permanganate ($MnO_4^-$). The advantage of using nitric acid is that it both adjusts the pH value downwardly and oxidises the sulfides as $No_3^-$ is also an oxidizing agent.

The reaction time of this first reaction is selected so as to ensure completion of the reaction, and the solution is then stripped with air for a given duration in order to remove bromine.

When increasing the potential of the solution at a given pH, the solution will pass through and beyond an area of the Pourbaix diagram in which colloidal elemental sulphur will be generated. Hence the reaction time and the duration of the air stripping step will be adjusted in order to insure that:

(i) all the elemental sulfur produced will be oxidized to sulfate and will consequently have no fouling effect downstream in the process;

(ii) all the bromine produced by this oxidation reaction will be stripped; and (iii) all the residual hydrocarbons and hydrogen sulfide will be stripped.

The chloride content is then measured by ionometry, using a special specific ion selective electrode.

The pH value does not need adjusting by any means other than the reaction with the oxidising reagent, so one oxidising reagent will suffice.

Figure 1:
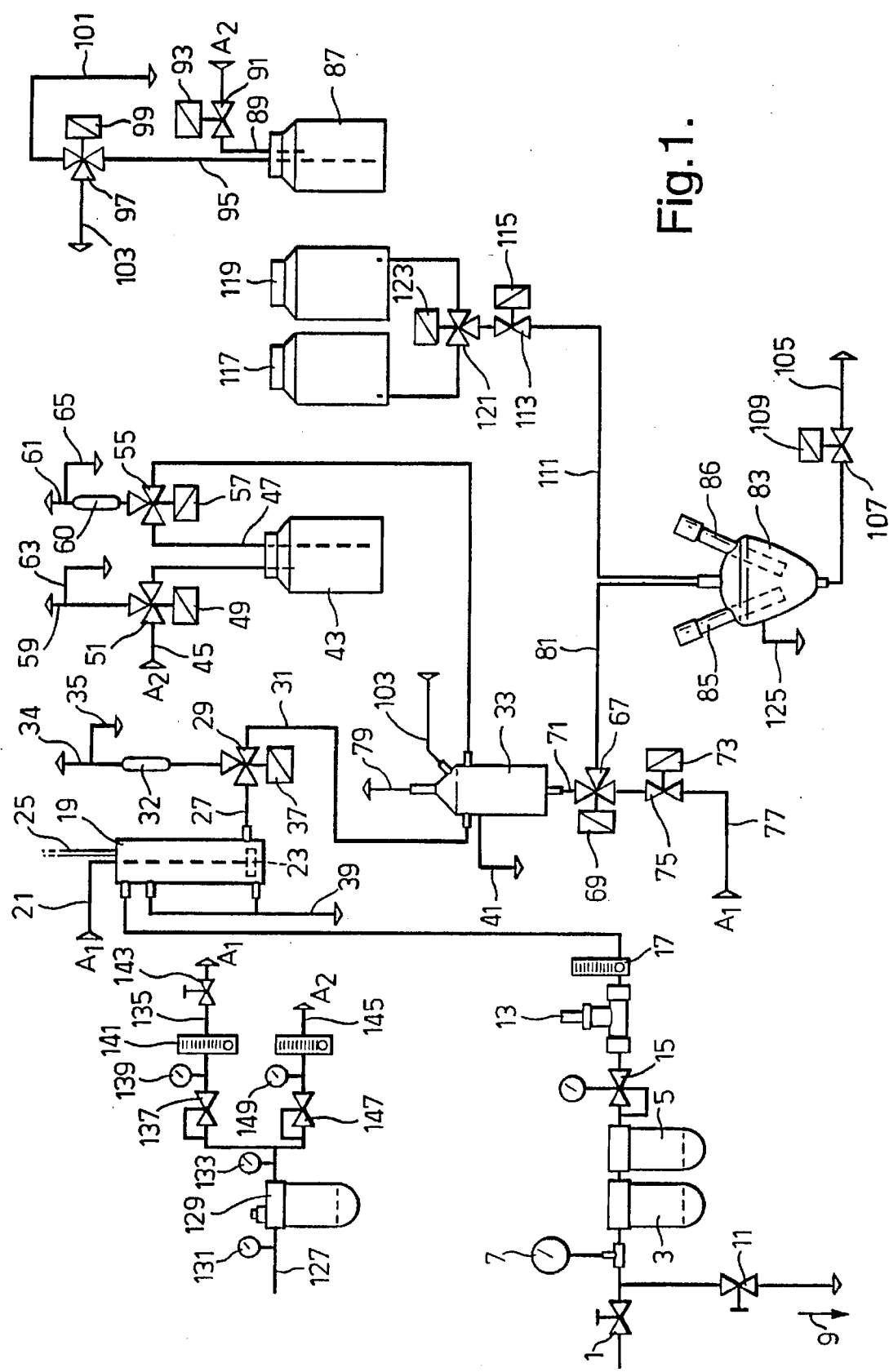
FIG. 1 is a schematic view of analysing apparatus for effecting the chloride analysis process in accordance with the present invention.

Referring now to FIG. 1 which shows an embodiment of the apparatus for carrying out the above method, there can be seen an inlet valve 1 adjustable to select a sample of a few hundred ml of process water to be passed to two successive water filters 3 and 5, the first filter 3 having a mesh size of 100 μm and the second filter 5 having a mesh size of 10 μm. In order to allow a small sample to be taken from the continuous flow rate passing through valve 1, excess process water from the valve 1 is passed to waste at 9 by way of a further control valve 11. Feed to the filters is by way of a thermometric sensor 7 which can be used as a means of protecting the analyzing apparatus against the effect of a high temperature sample by barring the further entry of such a sample beyond the inlet valve 1 or discharging it through valve 11.

Normally, adjustment of the flow rates set on the two valves 1 and 11 will control the flow rate of the process water passing through the two water filters 3 and 5.

From the second filter 5, the process water flows to a pH sensor 13, by way of a control valve 15. The pH signal may be used for identifying the position on the Pourbaix diagram as will be described below with reference to FIG. 2 but also provides a second parameter indicative of the corrosiveness of the sample batch of process water.

The flow of process water leaving the pH electrode 13 passes through a flow meter 17 on its way to a stripper column 19.

In the stripper column 19 air from a supply arrangement to be described later is introduced through inlet pipe 21 and released into the filtered process water through injector head 23. The air passing through the process water in the stripper column 19 the residual hydrocarbons and hydrogen sulfide and is discharged through a vent 25, whereas the stripped process water passes along line 27 to a three-way control valve 29 when a sample of the stripped liquid is being taken for advance along line 31 to a reactor vessel 33 of relatively small and controlled volume, in this case 25 ml.

During discharge of the stripper 19 the valve 29 will normally be connected, as shown, to communicate the discharge line 27 from the stripper with a vent line 34 for any entrained air therein and with an overflow line 35 for excess stripped process water.

This discharge from the stripper 19 proceeds until a vessel 32 in the line between the valve 29 and the overflow line 35, and that line itself, are full and stripped liquid begins to overflow through the line 35. For example, this operation may be controlled on a timed basis by a process control unit so that it will be known that the elapsed time during which the valve 29 remains in the position shown in FIG. 1 is sufficient to fill the vessel 32 and the line containing it.

At the appropriate time the valve 29 is then changed by being driven pneumatically in response to operation of its solenoid 37 to occupy a configuration in which it communicates the discharge line 27 from the stripper with the feed line 31 to the reactor vessel 33, in order to supply to that reactor vessel 33 a sample batch of stripped process water which is always of a precisely known volume (the volume of the vessel 32 and its line between the valve 29 and the overflow line 35).

To dispose of the surplus stripped process water while the controlled volume sample batch is passing out through the valve 29, there is a waste line 39 from the stripper column, communicating with both a top outlet and a bottom outlet thereof. When the sample batch has had time to pass through the valve 29 the solenoid 37 will again operate the valve 29 to communicate the stripper column discharge line 27 with the vent 34 and overflow 35.

In order to prevent overfilling of the reactor vessel 33, during cleaning (to be described later), and to avoid a build-up of excessive pressure therein, an overflow line 41 is connected to the reactor vessel in the upper part, thereby defining a constant liquid/air interface in the reactor vessel 33.

A single reagent, in this case an aqueous solution of nitric acid (1 mole/l) and sodium bromate (0.1 mole/l), is displaced from a reagent supply vessel 43 by means of air passing along line 45 from the above-mentioned air supply arrangement. The reagent leaves the supply vessel 43 through a discharge line 47 which dips into the vessel 43 well below the surface of the liquid therein. The reagent is caused to flow through discharge line 47 as a result of the application of air pressure above the upper level of the liquid in the supply vessel 43, once a solenoid 49 has operated a three-way flow valve 51 to communicate air supply line 45 with an air inlet line 53 to the reagent supply vessel 43. In order to control precisely the volume of reagent added to the reactor vessel 33, discharge from the supply vessel 43 is by way of a further three-way control valve 55, actuated by its solenoid 57, and associated with a volume control vessel 60, a vent 61 and an overflow 65 which are used in the same manner as the control vessel 32, vent 34 and overflow 35 described above. At all other times the three-way flow valves 51 and 55 will be maintained, by their respective solenoids 49 and 57, such that they communicate the reagent supply vessel 43 with vent lines 59 and 61 including waste bleeds 63 and 65 to isolate the reagent supply vessel 43 from the air supply line 45 and to guard against any possibility of back pressure from the reactor vessel 33 displacing reagent too far along the vent lines 59 and 61.

In practice the operation of the three-way flow valves 29 (directing the flow of stripped process water) and 51 and 55

(displacing and directing the flow of reagent) will be synchronised so that the stripped process water sample and the reagent will be simultaneously directed into the reactor at a rate which will give the desired concentration of the mix in the reactor. It is thus the restoration of the three flow control valves 29, 51 and 55 to the configurations shown in FIG. 1 which will trigger termination of the introduction of reactants into the reactor vessel 33.

During introduction of the reactants (reagent solution and filtered, stripped process water) into the reactor vessel 33 a three-way valve 67 will be controlled by its solenoid 69 to isolate the reactor vessel discharge line 71 from a feed line 81 to an ionometry cell 83. At the same time a shut-off valve 75 in an air supply line 77 to the three-way valve 67 is closed, thereby effectively closing off the discharge from the reactor vessel and allowing the reactants to collect in the reactor vessel 33. This condition of the valves 67 and 75 is maintained for a suitable reaction time interval after restoration of the three-way valves 29, 51 and 55 to the configuration shown in FIG. 1 where they have effectively closed off the flows of stripped process water and reagent to the reactor vessel 33. A time delay of the order of 10 minutes for the reaction in the reactor vessel 33 is adequate to allow oxidation of the sulfides in the sample of process water in the reactor vessel 33.

During the oxidation and acidifying reaction in the reactor vessel 33, the position plottable on the Pourbaix diagram moves, with simultaneous oxidation and acidification, along the straight line path AE across zone 84 on the Pourbaix diagram representing the deposition of elemental sulfur. This zone 84 is traversed without any interruption, and the reaction time is adjusted in order that, after zone 84 has been crossed, all the sulfur present will be oxidised into sulphate. Thus no elemental sulfur will reach the measuring cell.

Upon termination of the reaction, a solenoid 73 will operate the flow control valve 75 in the air supply line 77 to apply, to the three-way valve 67, air under pressure both to resist escape of the mixture from within the reactor vessel 33 and also to bubble the air through the reactor vessel 33 to a vent 79 in order to strip the mixture of reaction products in the vessel 33 of bromine. This bromine stripping operation can be carried out throughout the reaction time in the reactor vessel 33, and will be terminated by actuation of the solenoid 69 to operate the three-way valve 67 to communicate the reactor vessel 33 with the feed line 81 to the ionometry measuring cell 83 where determination of the chloride content of the prepared process water sample can be carried out by means of electrodes 85 and 86 of which electrode 85 is a reference electrode and electrode 86 is a specific ion selective electrode, selective in this case to chloride ions, to record the proportion of chloride ions present in the cell 83.

As will be understood from the above description, the air stripping phase will be initiated by opening of the flow control valve 75, after the desired reaction time in the reactor vessel 33, and will be terminated by operation of the three-way valve 67 to isolate the air supply from the reactor vessel 33 and to communicate the discharge line 71 with the measuring cell 83. This stripping phase may be of the order of 30 seconds, but will of course be adjustable in order to ensure adequate removal of the pollutants such as bromine, sulfides, and native sulfur which could interfere with the chloride measurement in the cell 83.

The result of the chloride analysis carried out using the electrodes 85 and 86 is then processed by a microprocessor, and is then preferably displayed and recorded for future study.

The whole of the operation described up to now is carried out automatically, under control of the microprocessor, at desired intervals and without any human involvement other than simply to ensure that the air supplies and power supplies are live. The cycle repeat frequency may be adjustable, for example from once per 20 minutes to once per 2 hours, and will be such that the batches are processed sequentially in rapid succession.

The control system to achieve this automatic operation of the device is not illustrated in detail in FIG. 1, but the design and construction of such a system is well within the ability of the skilled control engineer without requiring any additional inventive activity on his behalf in order simply to make the control system function as described.

The same control system also ensures that after a predetermined number of chloride analysis operations in the cell 83 an auto-calibration cycle will be carried out using standard solutions so as to ensure that the values recorded by the electrode system 85, 86 are still accurate. This auto-calibration operation will be described shortly below.

Furthermore, again after a number of chloride analysis operations, the control system will ensure that a controlled cleaning cycle is carried out automatically to clean the reactor vessel 33 and the measuring cell 83 using demineralised water from a demineralised water supply arrangement which will now be described.

The demineralised water supply arrangement illustrated in FIG. 1 comprises a demineralised water storage vessel 87 having an air supply line 89 which includes a control valve 91 actuated by a solenoid 93 to open the air supply at the start of a cleaning cycle. This application of air to the demineralised water storage vessel 87 initiates expulsion of demineralised water along an outlet line 95 to a three-way valve 97 which is controlled by a solenoid 99 and is normally in the condition illustrated in FIG. 1 in which communicates the water discharge line 95 with a waste line 101. The valve 97 is normally maintained in this open condition and will be held in that same configuration for a brief interval after the air supply line 91 is opened, thereby ensuring that demineralised water in the discharge line 95 and in the vicinity of the valve 97 is initially expelled to waste so that, when the solenoid 99 actuates the valve 97 to communicate the water discharge line 95 with a water supply line 103 to the reactor vessel 33, the initial flow of water will have been taken freshly from the demineralised water supply vessel 87.

During the cleaning cycle which is initiated by opening of the valve 97 to apply water to the line 103, the three-way valve 67 at the outlet from the reactor will be in the alternative configuration from that shown in FIG. 1 in that it communicates the discharge line 71 from the reactor with the feed line 81 to the measuring cell 83 and allows the discharge of the cleaning flow of demineralised water to a waste 105 by way of the measuring cell 83. This is permitted by actuation of a controllable dump valve 107 by its solenoid 109 to open to permit discharge flow, whereas normally during a measuring operation the valve 107 will be closed in order to ensure that a static sample of prepared process water in the measuring cell 83 can reside there long enough to allow the chloride measurement operation to take place. As indicated above, overfilling of the reactor vessel 33 is prevented thanks to the overflow line 41.

For the auto-calibration operation, the demineralised water flow to the reactor vessel 33 will normally be closed. During this auto-calibration cycle the measuring cell 83 will be supplied by way of a calibration supply line 111 from a flow control valve 113 actuated by solenoid 115.

In order to achieve adequate calibration, controlled volume samples of two standard solutions of different chloride concentration, together with equal volumes of the reagents from supply vessel 43, are introduced in succession, and are treated as though they were a sample of stripped process water tested in the way described above. For this purpose there are two reservoirs of standard solution, reservoir 117 including a mixture of process water and reagent with a residual chloride concentration of, in this case, 10 ppm and devoid of any hydrocarbons, sulfides and bromine, and the second reservoir 119 includes a similar solution but where in this case the chloride concentration is 100 ppm. When mixed with the volumes of reagent these solutions in the ionometry cell 83 will have final chloride concentrations of 5 ppm and 50 ppm, respectively. However, the concentrations of the standard solutions (10 and 100 ppm) in the reservoirs 117 and 119 can be adjusted as required in order to correspond to the likely chloride concentrations in the process water to be monitored thereby ensuring that the autocalibration always takes place in the working concentration range. For example, if the chloride concentrations which the apparatus is to be expected to monitor are of a higher or a lower value than the range of from 10 to 100 ppm, correspondingly higher or lower chloride concentrations will be present in the standard solutions in the reservoirs 117 and 119.

Selection of the appropriate one of these pre-prepared solutions is achieved by way of a three-way valve 121 actuated by a solenoid 123. In the configuration shown in FIG. 1 it is the reservoir 117 whose 10 ppm solution is about to be gravity fed to the measuring cell 83 once the shut-off valve 113 is opened. This cell-loading operation will occur until the appropriate controlled volume of the standard 10 ppm solution has been introduced, at which time the valve 113 will be closed to stop flow of the solution. Substantially simultaneously the controlled volume of reagent is added. A measuring cycle of the desired duration can then be carried out using the electrodes 85 and 86, during which time the valve 121 may be actuated by its solenoid 123 to communicate now the reservoir 119 with its stronger (100 ppm) solution with the shut-off valve 113.

At the end of the measuring operation, when the error (if any) between the measured value and the known chloride concentration of 10 ppm has been recorded, the dump valve 107 is opened and the contents of the measuring cell 83 are discharged to empty the cell 83 ready for the next part of the auto-calibration cycle when the dump valve 107 is closed and the calibration flow valve 113 is opened to load the measuring cell 83 with a desired quantity of the 100 ppm solution from the reservoir 119 after which the closure of the calibration flow valve 113 defines the end of that sample and signals that the measuring cell 83 is ready for its second calibration stage. As before, the error (if any) between the recorded concentration and the known value of 100 ppm chloride content is noted and, on the basis of the two error readings (one at 10 ppm and one at 100 ppm) any adjustment of the calibration of the apparatus can be carried out.

Preferably such an auto-calibration adjustment is effected fully automatically by way of the same microprocessor which controls the timing and the data-processing resulting from a typical measurement operation on a non-standard process water sample as described above, in order to correct for any drift in the measurement system.

Optionally, the measuring cell and its discharge line 105 can be purged between each measuring phase by opening the air shut-off valve 75 to communicate the reagent stripping air feed line 77 with the three-way valve 67, and at the same time operating the three-way valve 67 to communicate the air shut-off valve 77 with the feed line 81 to the measuring cell 83. This will allow any residue of the previously analysed liquid to be discharged from the bottom of the measuring cell by way of the dump valve 107 and waste line 105, following which the dump valve 107 can again be closed ready for the next measuring cycle. This can occur equally between successive sample measuring cycles, or between the two parts of a calibration cycle, or between the auto-calibration cycle and the nearest preceding or succeeding process water sample measuring cycle.

In order to guard against overpressure in, or overfilling of, the measuring cell 83, it is provided with an overflow line 125.

The air supply arrangement referred to above is also illustrated in FIG. 1 and comprises an air inlet line 127 supplying air at a pressure in excess of the greatest propulsion air or pneumatic drive air flow. The air supply pressure is, for example, 6 bar gauge pressure and is preferably also used, without pressure step-down, to control the various solenoid-operated shut-off valves 75, 91 and 113, and the solenoid-operated three-way valves 29, 51, 55, 67, 97 and 121. In each case the solenoid drives a shuttle valve which then controls the application of air at, for example, 6 bars pressure, to drive the shut-off valve or rotary valve between its two operating positions.

The air from main air supply line 127 passes through an air filter 129 upstream and downstream of which are pressure gauges 131 and 133, respectively.

After the second pressure gauge 133, which provides a check on the pressure of the filtered air, the air flow splits between first and second partial flow air lines 135 and 145.

Air passing along line 135 passes through a throttle valve 137, a pressure monitoring transducer 139, a flow meter 141, and a throttle valve 143 to constitute flow $A_1$ at a lower pressure which is adequate to drive fluid through the various elements of the apparatus. In this particular case the air flow $A_1$ is used at air supply line 21 to the stripper 19, the reagent stripping air line 77, and the demineralised water propulsion air line 89. A typical pressure for these uses has been found to be 50 millibars.

Air flowing along the second air flow line 145 passes by way of a throttle valve 147, a pressure transducer 149, and a flow transducer 151 to form a pneumatic drive air flow $A_2$ which is used for the reagent propulsion air line 45 and the demineralised water propulsion air line 89 for the cleaning system.

As examples of commercially available equipment which can be used for components of this apparatus, we can mention the possibility of using for the specific ion selective electrode 86 a combined electrode type CE9417B marketed by the Orion Company.

Figure 2:
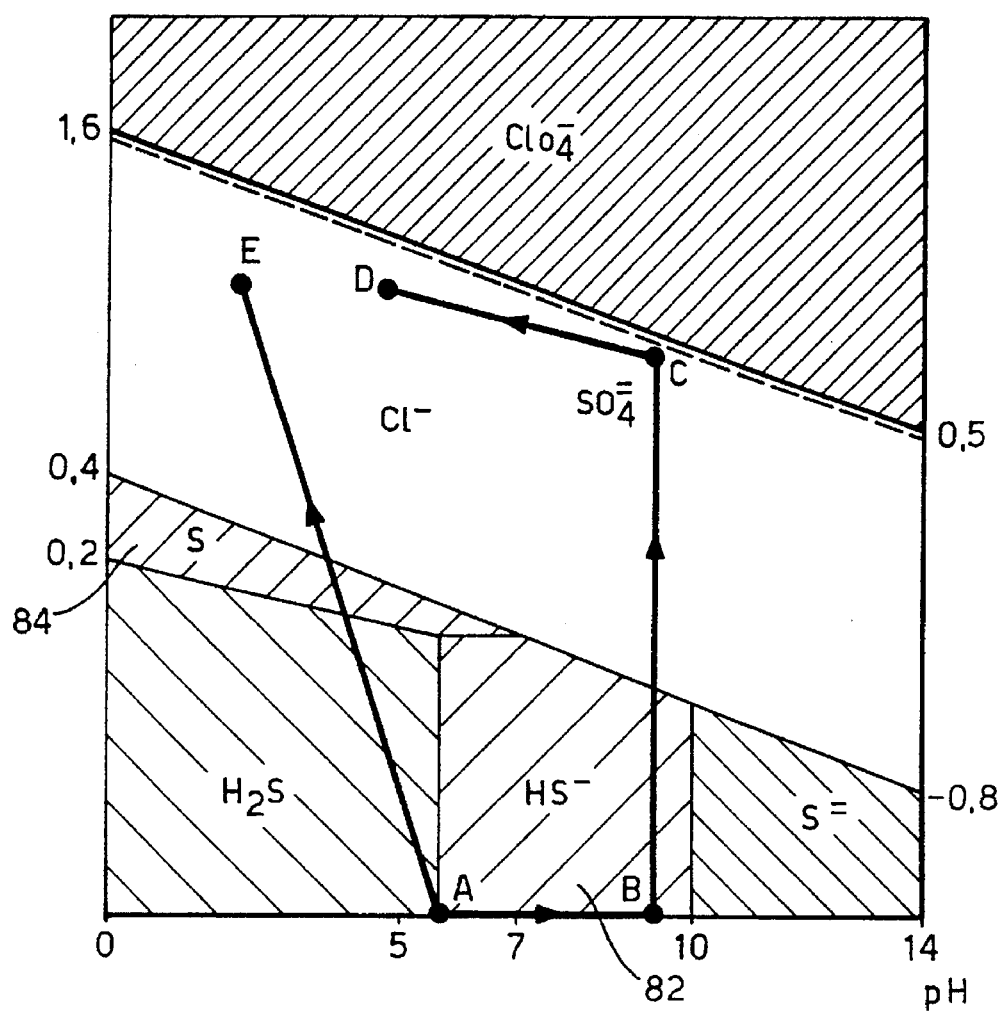
FIG. 2 is a Pourbaix diagram plotting potential against pH value during the execution of the embodiments of process described herein.

FIG. 2 shows the Pourbaix diagram for the process carried out using the above described apparatus. The likely pH value of the process water sample to be tested is from 4 to 9, and the arrangement is preferably one in which the pH is low (i.e. in the acidic range), and the injection of caustic to reduce the acidity may be avoided, so that the passage through the Pourbaix diagram follows the straight line AE of FIG. 2 and gives a relatively direct route into the unhatched region beyond (above) the zone 84 in which elemental sulfur may be generated. The circuitous route ABCD is the obvious one to be followed in order to avoid deposition of elemental sulfur (S) in the zone 84, by avoiding the zone 84 altogether, as in U.S. Pat. No. 4,942,133. However, this circuitous route requires the addition of caustic in order to reduce the acidity to arrive at the point B as a way of avoiding generation of elemental sulfur and the major part of the $HS^-$ generation zone 82. The point D obtained by the circuitous route could even be chosen to coincide with point E on the Pourbaix diagram as shown in FIG. 2, without the route ABCD involving the deposition of elemental sulfur. The straight line route AE arrives at a location well into the region between the sulfur and chloride generation regions in a more direct manner and, although some elemental sulfur will be generated, it will be oxidised in the reaction (due to an excess of reagent) so that it can then be readily stripped in the air stripping operation occurring in the reactor vessel 33 after the oxidation reaction. This allows the overall process time to be considerably reduced, and in practice the resultant measure of chloride concentration is available just over half an hour from the time of collecting the sample. Furthermore, because the apparatus in accordance with the present invention is self-contained and automatic in operation it can be installed in situ in the plant and does not require the sample to be conveyed away for subsequent and remote analysis. This possibility of mounting the analysis apparatus on site is enhanced by the auto-calibration and self-cleaning characteristics of the device as described above, all carded out under control of its microprocessor.

The measurement carried out in the ionometry measuring cell 83 is particularly reliable due to the fact that there is no bromine present after the stripping in the reactor vessel 33, and due to the frequent calibration of the device by means of the auto-calibration feature. Furthermore, the stripping step in stripper column 19 avoids the presence of sulfur-liberating sulfides in the process water being prepared and analysed, so there is no poisoning of the electrode and hence there will be a stable reliable measurement facility.

All of the water movement is achieved by way of air pressure motivation, thereby avoiding the need for pumps to be in contact with the low pH liquids. Furthermore, the short analysis time (of the order of 10 minutes) in the ionometry measuring cell 83 avoids degradation of the specific ion selective electrode 86 which could occur if the process were carried out continuously and the electrodes 85 and 86 were then spending a long time in contact with an aggressive medium.

It has been found that the auto-calibration and self-washing features of the apparatus and process described above lead to the possibility of maintenance work being carried out only once every three months, thus making the apparatus much more attractive commercially than one which requires human control and frequent maintenance and cleaning.

In the past there have been attempts, such as in U.S. Pat. No. 4,942,133, to produce a continuous chloride measurement system in the refinery or petrochemical industry, but the use of a discontinuous process with a relatively short cycle time and with cycles repeated at frequent intervals as described above gives rise to a reduced reagent cost and also allows the auto-calibration and self-washing features of the system disclosed herein.

The process of the present invention constitutes a distinct improvement over that of U.S. Pat. No. 4,942,133 in that the present invention requires only one reagent whereas there were two reagents used in U.S. Pat. No. 4,942,133.

Surprisingly, we have found that avoiding the quest for continuous on-line operation enables the process and apparatus of the present invention to be operated quite satisfactorily and to be used in a closed loop system which alters the dosage of a conditioning additive, for example caustic or a corrosion inhibitor, to a liquid with a sufficiently rapid response time to control the effect of the conditioning additive, for example in the present case where the conditioning additive is a corrosion inhibitor and the corrosiveness of the process waters in the refinery or petrochemical industry is to be kept within limits.

The electrical output of the microprocessor-control system which indicates the concentration of chloride ions in the ionometry cell can be compared, again by the microprocessor, with the desired stable reading and any difference between the two values can be used either to increase, or to decrease (as necessary), the rate of addition of conditioning additive. The process thus operates in a closed loop, preferably with a continuous addition of conditioning additive and a batchwise analysis of the chloride content.

As a further refinement, the output of the pH sensor 13 may also be monitored by the microprocessor in order to provide a double check on the effectiveness of the introduction of conditioning additive to maintain corrosiveness within limits. The principal control action is in response to the chloride concentration, and monitoring the pH provides a continuous verification of the effectiveness of the chloride concentration-dependent correction of dosage rates.

As indicated above, the frequency of repeating the analysis cycle may be adjustable, for example to give repeat rates of one every 20 minutes up to one every two hours. The shortest repeat rate will be substantially equal to the minimum duration of the analysis sample so that one analysis cycle starts as the preceding one just finishes, although in practice because of the batchwise treatment using (a) the stripper 19, (b) the reactor vessel 33 and (c) the ionometry cell 83 it is conceivable that the cycles may overlap slightly so that while one sample is being subjected to the ionometry operation in cell 83 the next sample may already enter the stripper 19 to prepare it for introduction to the reactor vessel 33.

Figures 3, 3A, 3B:
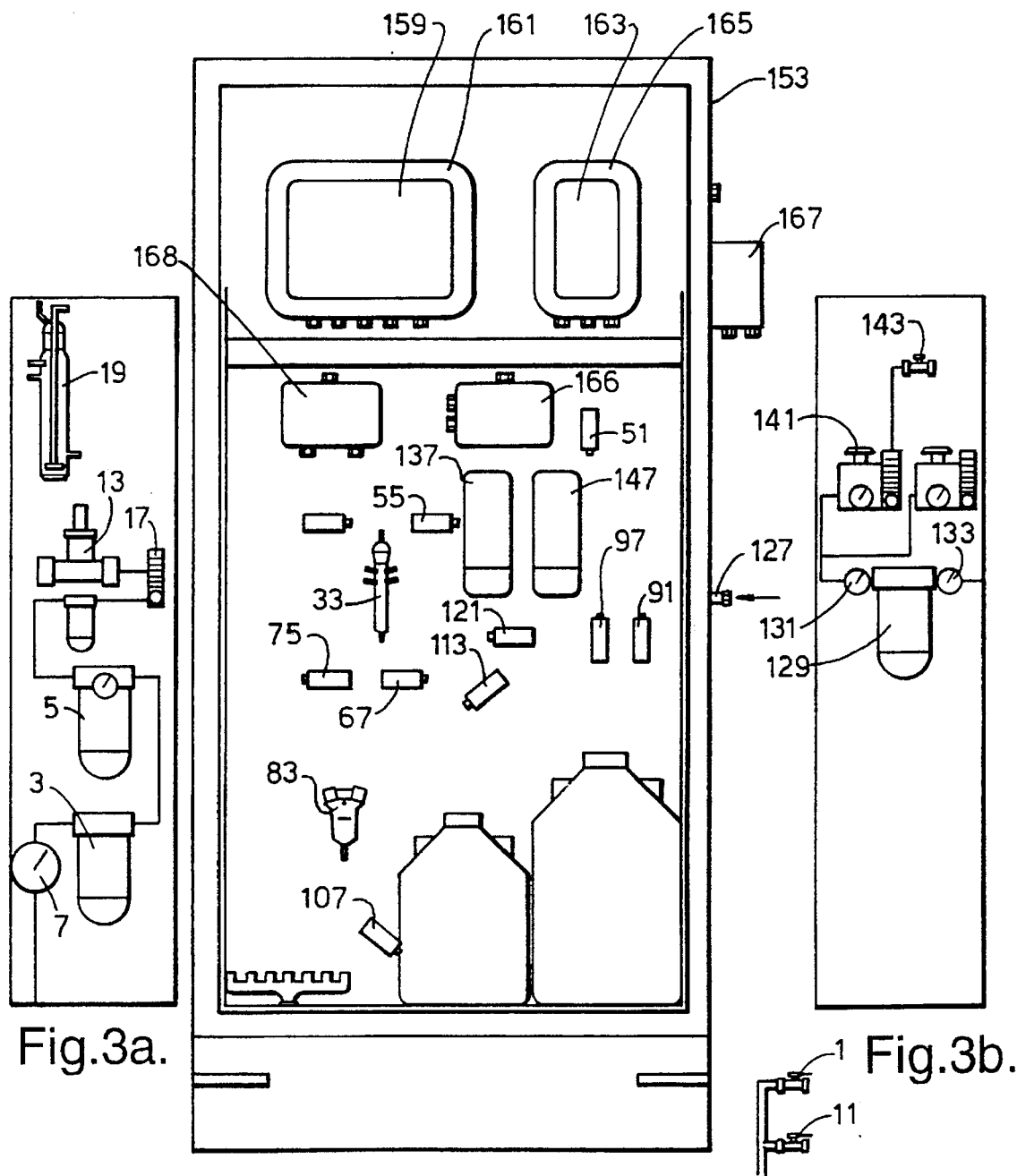
FIG. 3 is a front view of the lockable cabinet containing the apparatus, with the door open.
FIG. 3a is a view of the interior of the left-hand side wall of the cabinet.
FIG. 3b is a view of the interior of the right-hand side wall of the cabinet.

FIG. 3 shows the layout of the principal components of FIG. 1 in which the same reference numerals are used, although there is no illustration of the interconnecting fluid lines. The components visible in FIG. 3 are those which are mounted on the rear wall of the lower portion of the cabinet but below the shelf 157. The components shown above the shelf 157 are the control unit 159 incorporating the microprocessor, within the explosion-proof enclosure 161, and the junction box 163 within its own explosion-proof enclosure 165. Most of the high voltage electronic components are enclosed within the enclosures 161 and 165, and the remaining electronic components below the shelf 157 are in explosion-resistant housings 166 and 168. All other compounds are all linked pneumatically or hydraulically, or incorporate low voltage solenoids which are connected to the junction box 163 by low voltage lines on which no spark risk will occur.

FIG. 3a shows those components which are mounted on the left-hand wall of the cabinet 153, in principle the various water inlet pipes, filters and sensors as well as the stripper column 19, and FIG. 3b shows the various components of the air supply which are mounted on the right-hand inner wall of the cabinet 153.

The cabinet 153 is lockable and is connected to the on-site surfaces simply by the air inlet 127, the water inlet 155, and an electrical switch 167 on the exterior of the cabinet.

All electronic components having a spark risk are located within the enclosures 161 and 165 which are explosion-proof. Furthermore, there are no electric motors which could give rise to sparks and could therefore result in explosion risk on the side, as all liquid propulsion is pneumatically-induced.

Figure 4:
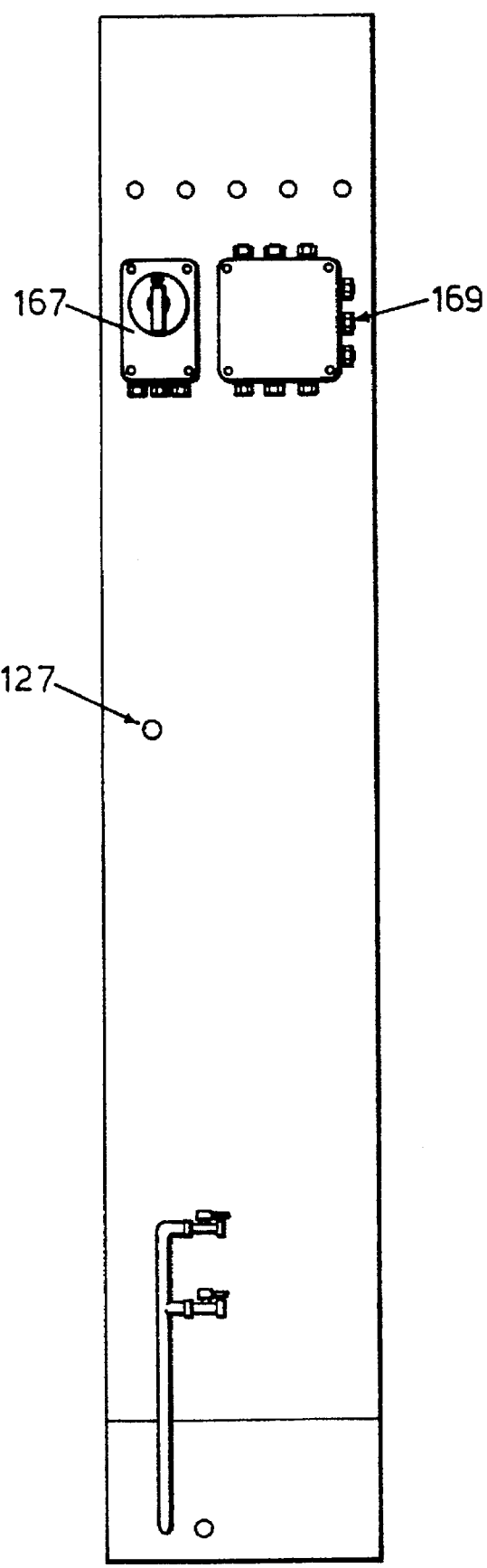
FIG. 4 is an exterior view of the right-hand side of the cabinet.

FIG. 4 is an elevational view of the right-hand side of the cabinet 153 and shows the air inlet 127 and the main switch 167 as well as the main electrical connector box 169 on the outside of the cabinet.

Figure 5:
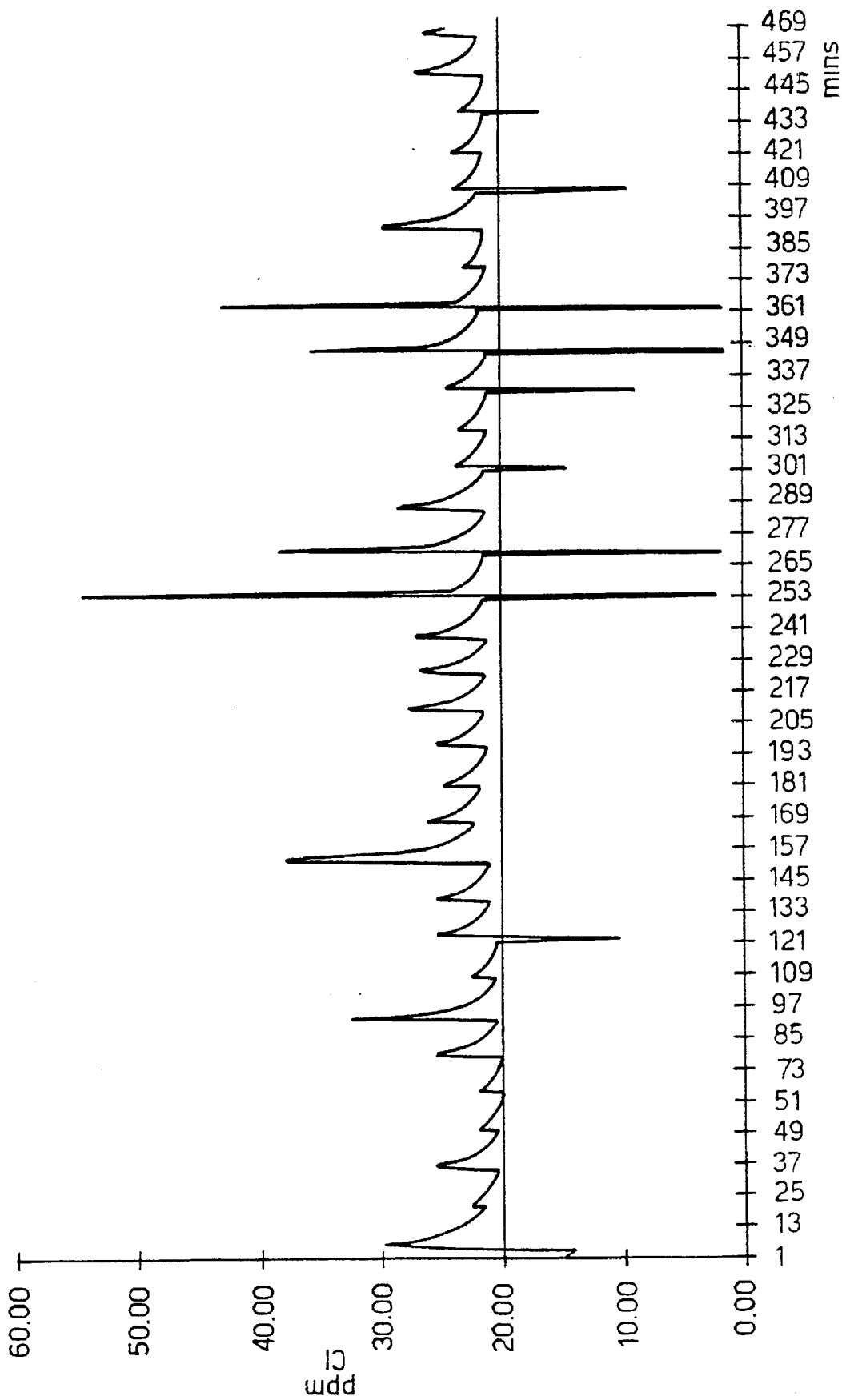
FIG. 5 is a plot of the chloride concentration in ppm over a prolonged period in minutes covering several measuring cycles.

FIG. 5 shows a typical plot, obtained in practice, of the ionometry cell output signal during a succession of batch-wise measuring cycles with a repetition frequency of 12 minutes.

As can be seen from FIG. 4, when the reaction products first enter the ionometry cell 38 the ionometry electrode output signal rises to a high value resulting from the upset of the change of sample, and then progressively return to a stable output at the end of the cycle. This minimum "stable output" signal is the value which is taken by the microprocessor as the actual chloride concentration and, as can be seen from FIG. 4, the value is in practice substantially 20 ppm.

Any attempt to operate on a continuous on-line basis results in an inability to derive a satisfactory value because of this upsetting influence of the sample change on the chloride concentration output signal. We have found that by avoiding the obvious tendency to aim for an on-line continuous process we are able to extract the minimum "stable output" value from the chloride concentration signal over the cycle and derive what is an accurate indication. This can be verified by deriving the output signal during an auto-calibration cycle when the same pattern of a disturbed high signal settling down to a "stable output" minimum value can be seen, but with different concentration values of 50 ppm and 5 ppm during the pans of the auto-calibration cycle.

In FIG. 4 the abscissa is a measurement of time in seconds and the ordinate is the chloride concentration in ppm.

We claim:

1. Apparatus for analyzing the chloride content of liquid, comprising: stripper means to receive said liquid to be analyzed and to strip compounds from the liquid by passing stripping air through the liquid;

a batch reactor vessel connected to said stripper to receive the stripped liquid and also connected to a supply of a chloride detecting reagent for reaction with said liquid;

an ionometry measuring cell for measuring the chloride content connected to receive the reaction product from said reaction vessel;

air propulsion means for propelling the liquid and reagent through the apparatus, thereby avoiding the need for pumps in contact with the liquid being analyzed;

control means for controlling the charging and discharging of successive batches of liquid in said stripper, the reaction in said reactor vessel, and the ionometry operation in said ionometry cell; and including an air supply source adapted to energize pneumatically-driven control valves of the apparatus, and to supply a pressure reduction system to ensure the availability of reduced pressure air for said air propulsion through the apparatus; wherein said pressure reduction means includes first and second separate pressure reducers, said first pressure reducer generating a flow of stripping air to be passed through the liquid being prepared for analysis, and said second pressure reducer generating said propulsion air at a pressure above that of the stripping sir but lower than that of the system air used for controlling the valves.

2. Apparatus according to claim 1, and further including means for periodically cleaning the reactor vessel and the ionometry measuring cell after a predetermined plural number of ionometry analysis cycles and for controlling the duration of such a cleaning operation.

3. Apparatus according to claim 1, and further including electrical and/or electronic components, wherein all of said electrical and/or electronic components which are liable to create a spark or other explosion risk are housed in one or more explosion resistant housings and all other components of the apparatus are outside said explosion resistant housings.

4. Apparatus according to claim 1 and further including control means for admitting liquid to said stripper vessel, initiating application of stripping air to said stripper vessel, passing said stripped liquid, from said stripper vessel to said reactor vessel, communicating said reactor vessel with said reagent supply and urging reagent from said supply into said reactor vessel, and communicating said reaction products with said ionometry measuring cell on completion of the reaction in said reactor vessel.

5. Apparatus according to claim 4, and further including means for introducing stripping air into said reactor vessel after a predetermined reaction time has elapsed, for stripping a constituent of the reaction products in said reactor vessel.

6. Apparatus according to claim 1, and further including a pH sensor in the feed to said stripper vessel.

7. Apparatus according to claim 6 and further including filter means in said supply line for liquid to said reactor vessel.

8. Apparatus according to claim 1, and including means for periodically auto-calibrating the ionometry measuring cell by introducing pre-prepared solutions of known chloride concentration into said cell and controlling an automatic analysis operation to verify the accuracy of the ionometry or to establish the error in said ionometry.

9. Apparatus according to claim 8 and including means for adjusting the processing program to correct for drift ascertained during said auto-calibrating operation.

10. Apparatus according to claim 9, wherein said auto-calibrating operation means includes means for selecting sequentially different supplies of different said pre-prepared solutions with differing chloride concentrations and for carrying out sequential determine the error at the various different chloride concentration levels.

* * * * *